United States Patent
Mathias et al.

(10) Patent No.: US 6,520,948 B1
(45) Date of Patent: Feb. 18, 2003

(54) SAMPLING TUBE HOLDER FOR BLOOD SAMPLING SYSTEM

(75) Inventors: Jean-Marie Mathias, Lillois (BE); Thomas Walter Coneys, Saint-Doulchard (FR)

(73) Assignee: Baxter International Inc., Deerfield, IL (US)

(*) Notice: Subject to any disclaimer, the term of this patent is extended or adjusted under 35 U.S.C. 154(b) by 0 days.

(21) Appl. No.: 09/492,060

(22) Filed: Jan. 27, 2000

Related U.S. Application Data

(63) Continuation-in-part of application No. 09/364,628, filed on Jul. 29, 1999, now Pat. No. 6,387,086.

(51) Int. Cl.[7] .............................................. A61B 19/00
(52) U.S. Cl. .................................... 604/409; 604/6.15
(58) Field of Search ................................ 604/403, 406, 604/407, 408, 409, 410, 411, 4.01–5.01, 6.15, 262; 206/438; 128/DIG. 24

(56) References Cited

U.S. PATENT DOCUMENTS

| | | |
|---|---|---|
| 2,460,641 A | 2/1949 | Kleiner |
| 3,469,572 A | 9/1969 | Nehring |
| 3,494,352 A | 2/1970 | Russo et al. |
| 3,817,240 A | 6/1974 | Ayres |
| 3,890,203 A | 6/1975 | Mehl |
| 3,931,815 A | 1/1976 | Takatsuki |
| 4,121,585 A | 10/1978 | Becker, Jr. |
| 4,320,769 A | 3/1982 | Eichhorn et al. |
| 4,325,369 A * | 4/1982 | Nilson ........................ 604/214 |
| 4,867,172 A * | 9/1989 | Haber et al. ................ 600/576 |
| 4,943,283 A * | 7/1990 | Hogan ........................ 604/198 |
| 5,033,476 A | 7/1991 | Kasai |
| 5,259,841 A * | 11/1993 | Hohendorf et al. ......... 604/110 |
| 5,360,012 A * | 11/1994 | Ebara et al. ................ 422/100 |
| 5,496,281 A * | 3/1996 | Krebs .................... 604/168.01 |
| 5,496,301 A | 3/1996 | Hlavinka et al. |
| 6,126,618 A | 10/2000 | Bischof |

FOREIGN PATENT DOCUMENTS

| | | |
|---|---|---|
| EP | 0 334 956 A1 | 10/1989 |
| EP | 0 537 863 B1 | 4/1993 |
| FR | 2 655 532 A1 | 8/1991 |
| WO | WO 00/06225 | 2/2000 |

* cited by examiner

*Primary Examiner*—Brian L. Casler
*Assistant Examiner*—Catherine Serke
(74) *Attorney, Agent, or Firm*—Andrew Kolomayets; Michael C. Mayo

(57) ABSTRACT

A holder for receiving a sampling tube of a blood sampling system is disclosed. The holder has an interior pocket which can be conformed from a closed position to an open position for receiving the sampling tube.

26 Claims, 14 Drawing Sheets

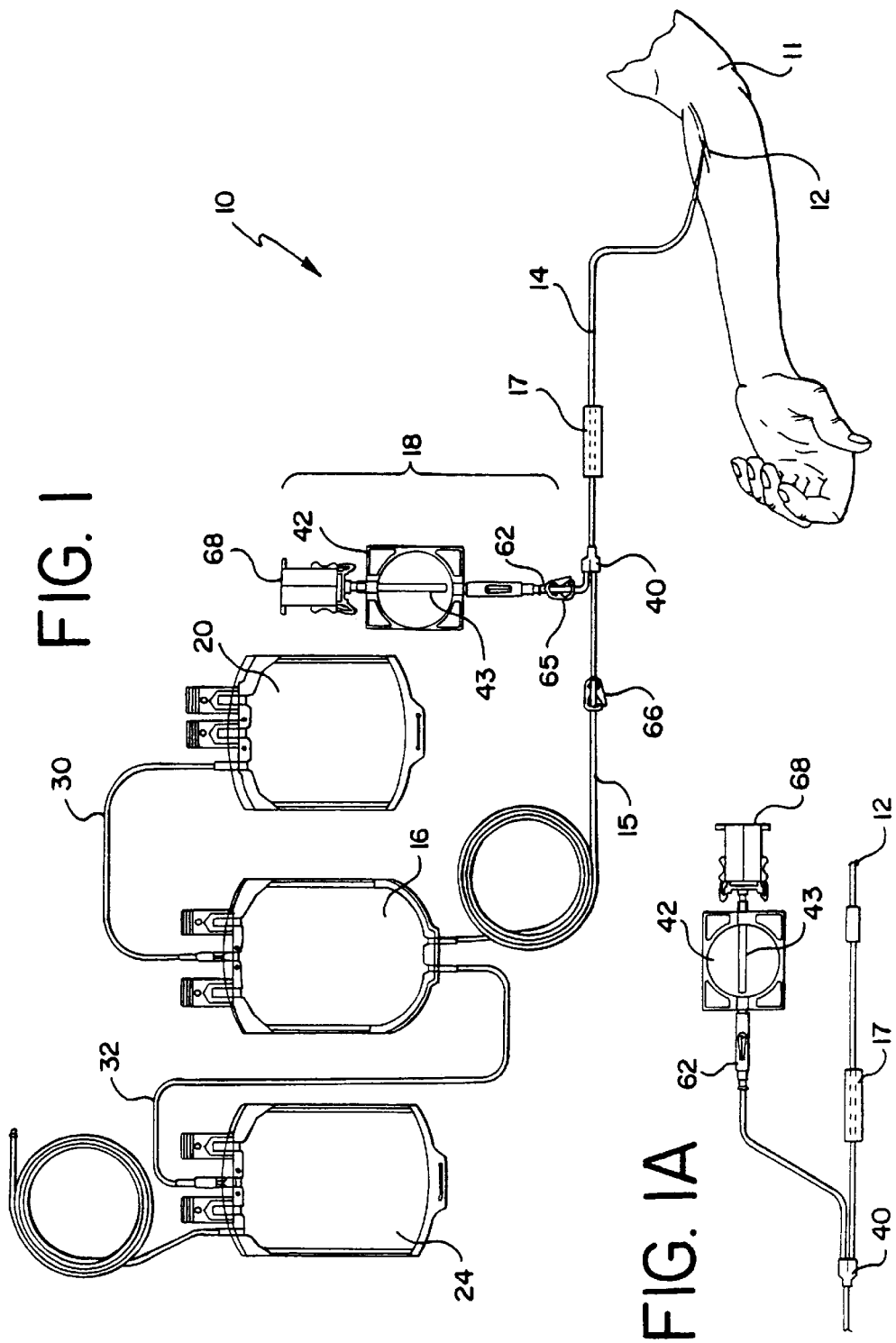

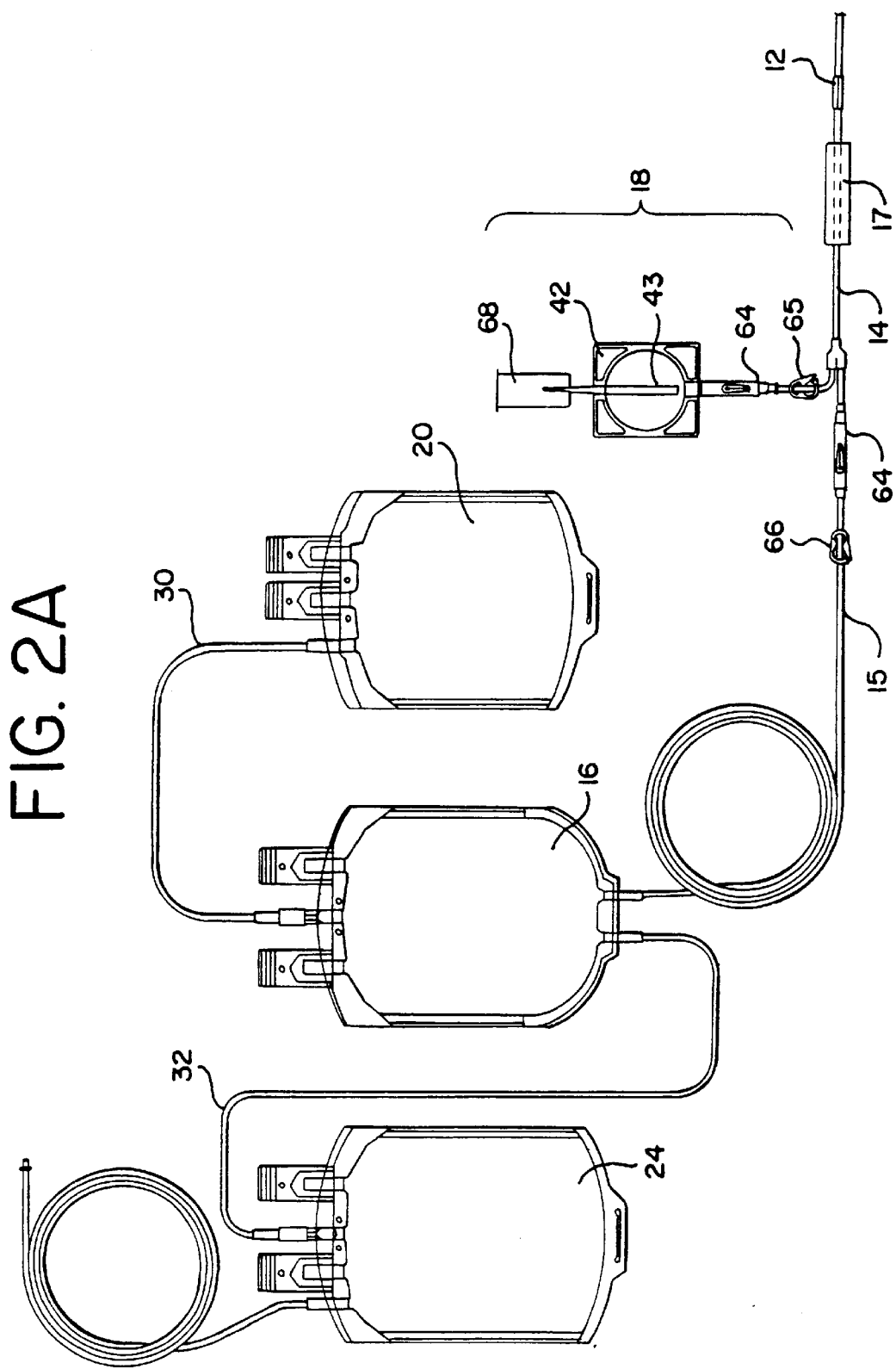

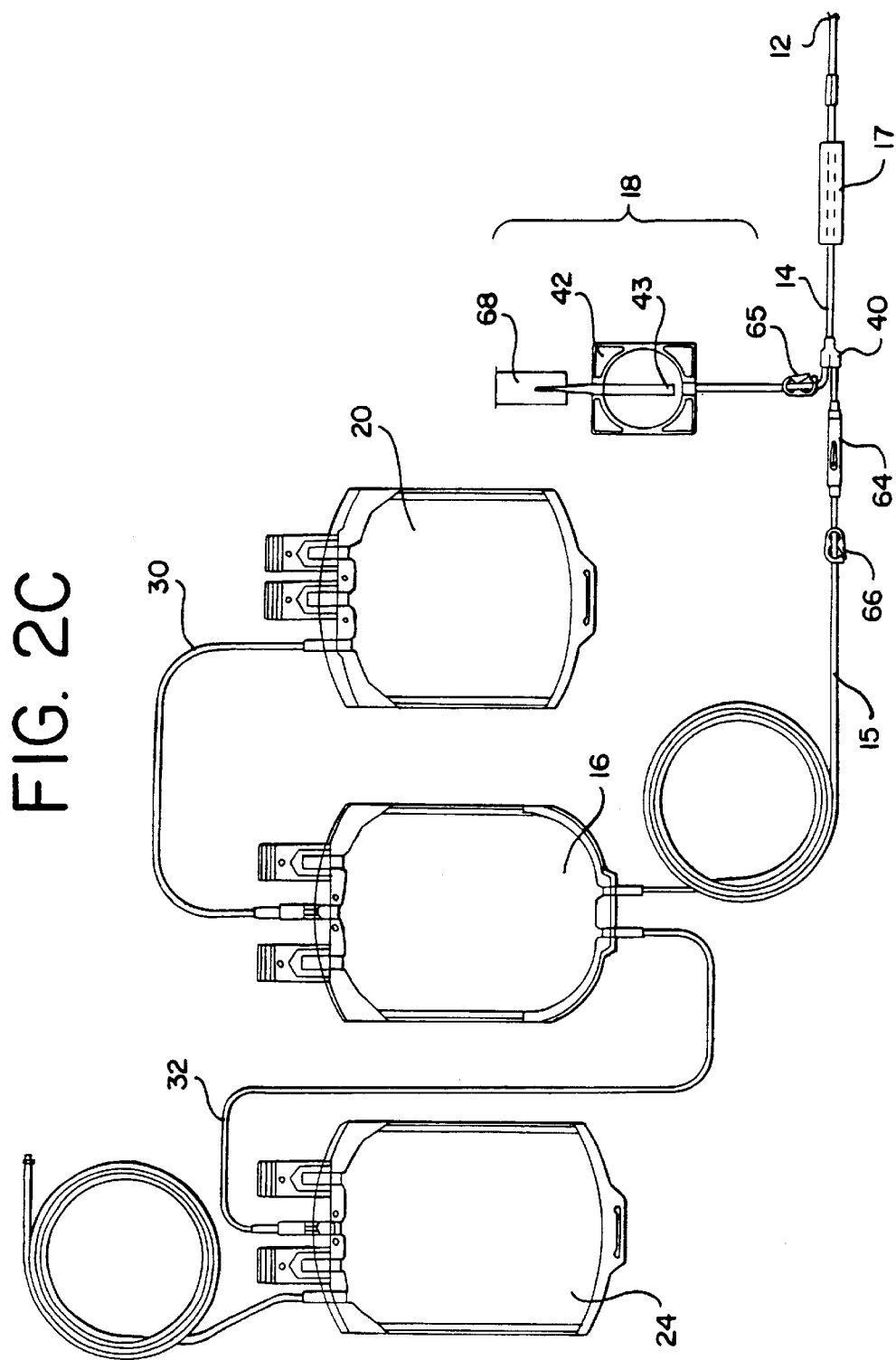

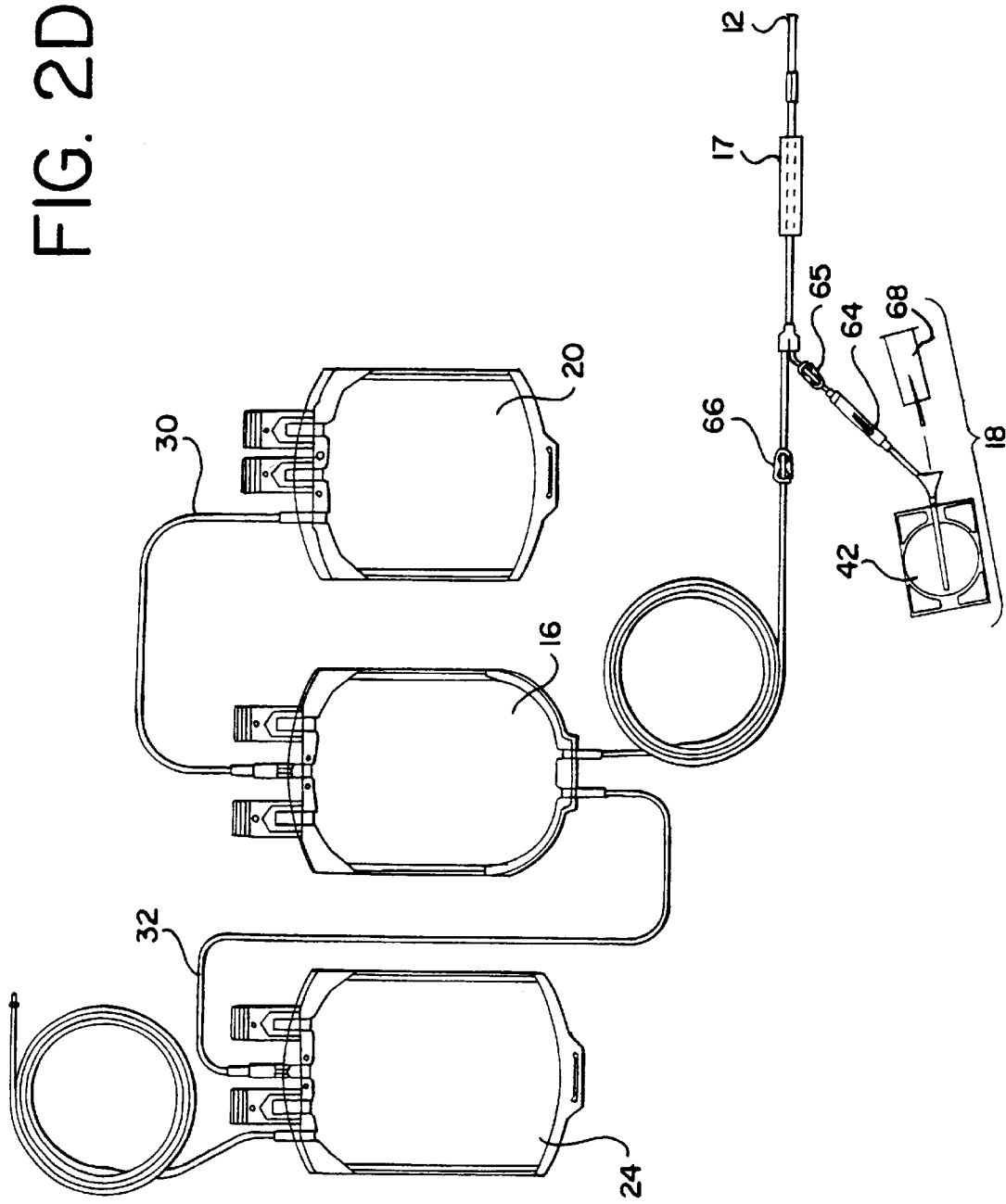

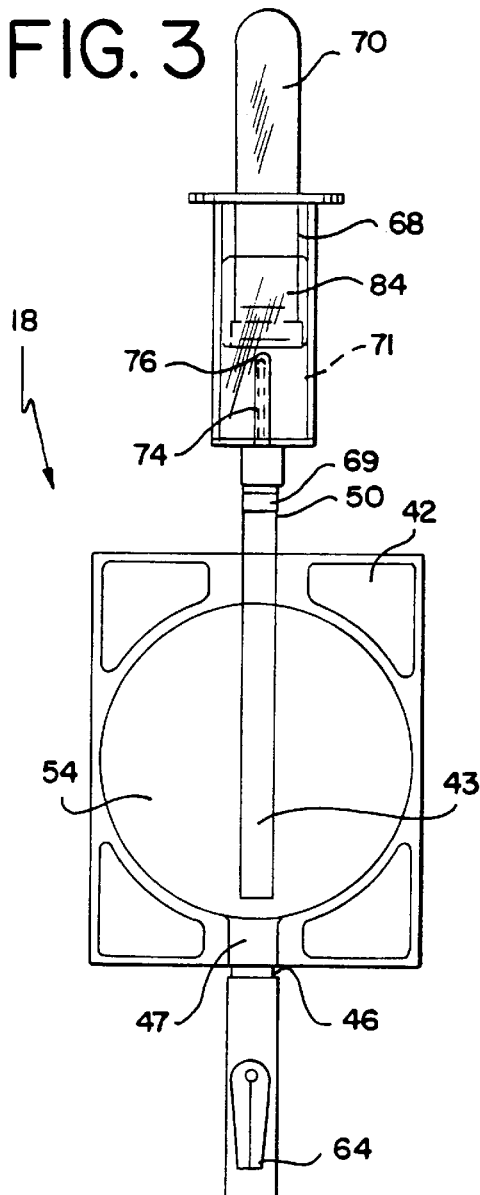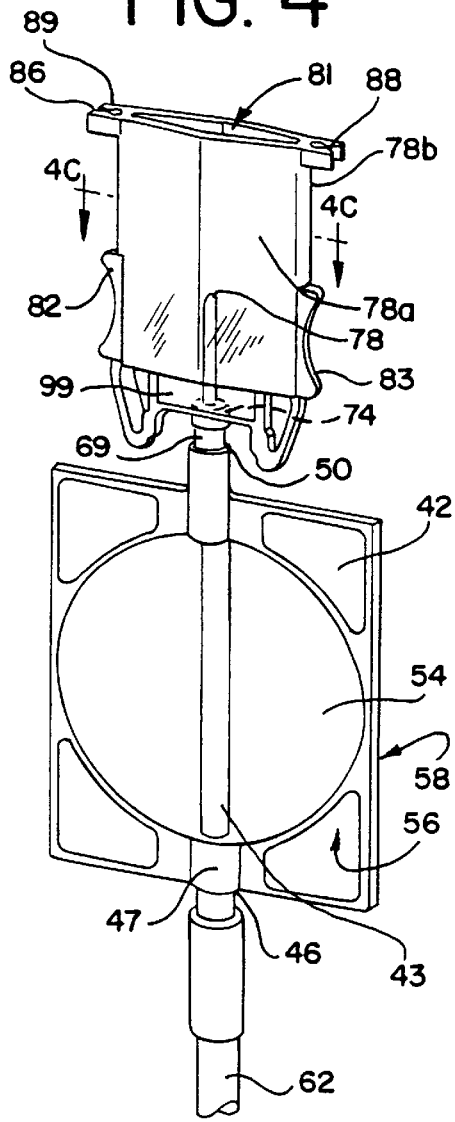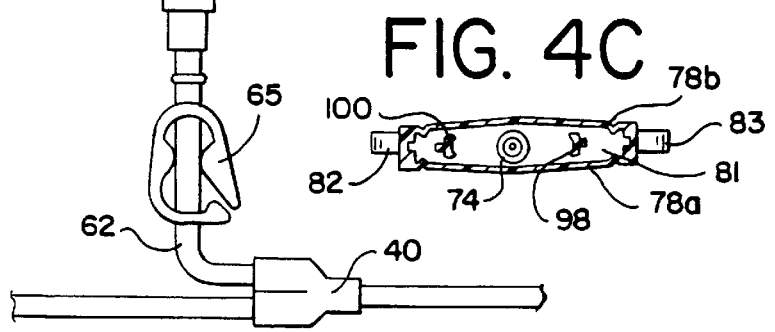

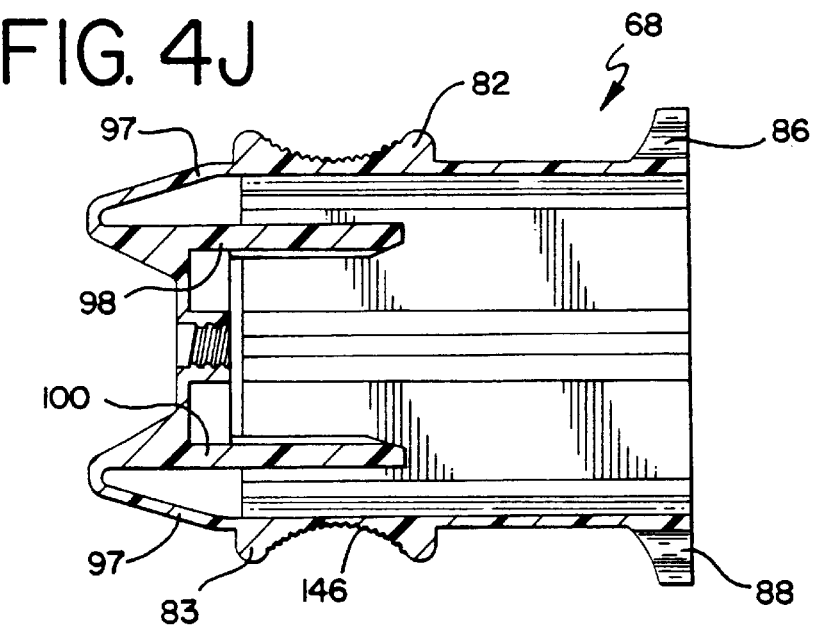
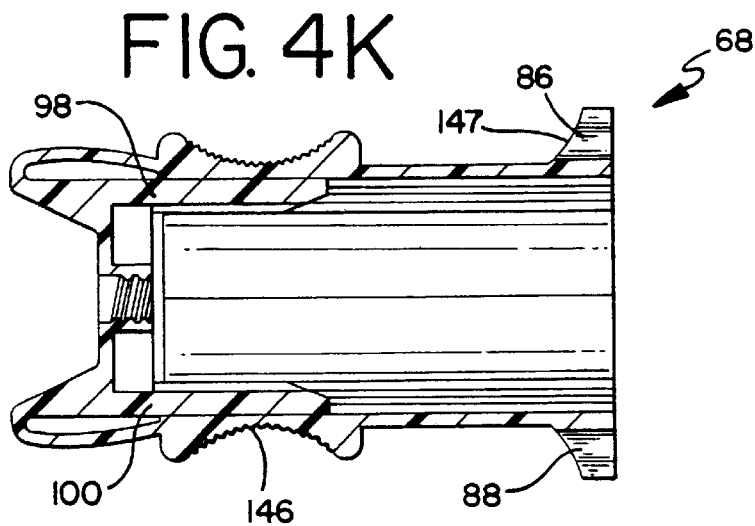
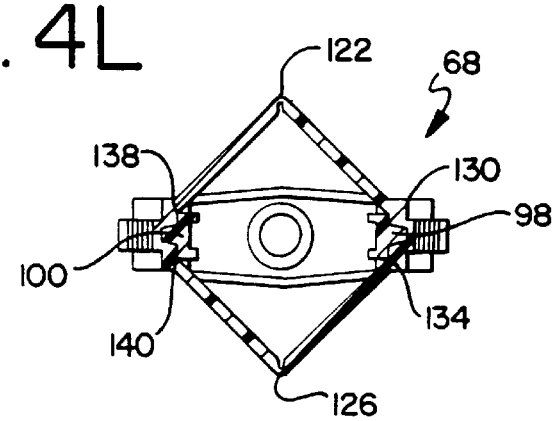

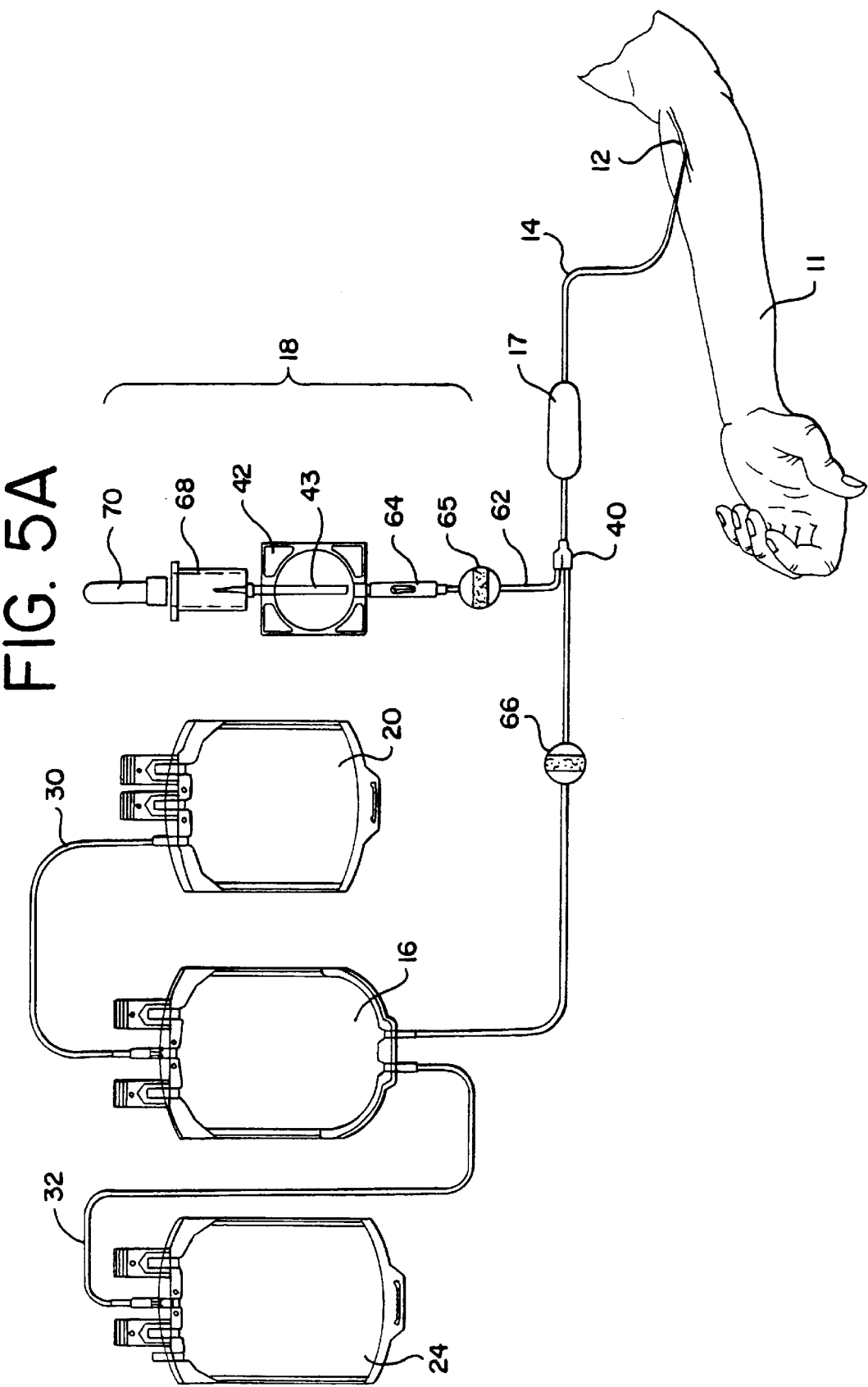

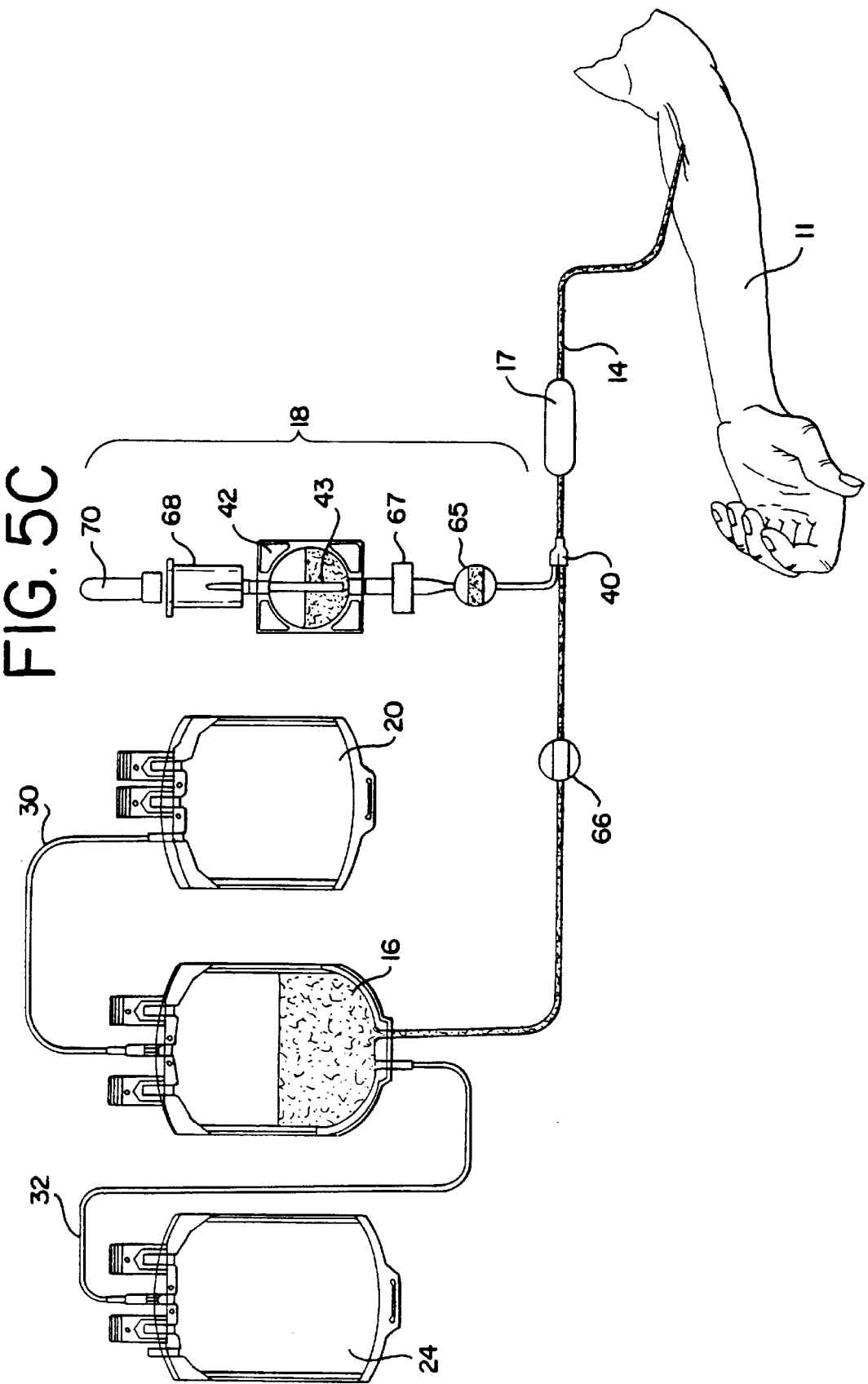

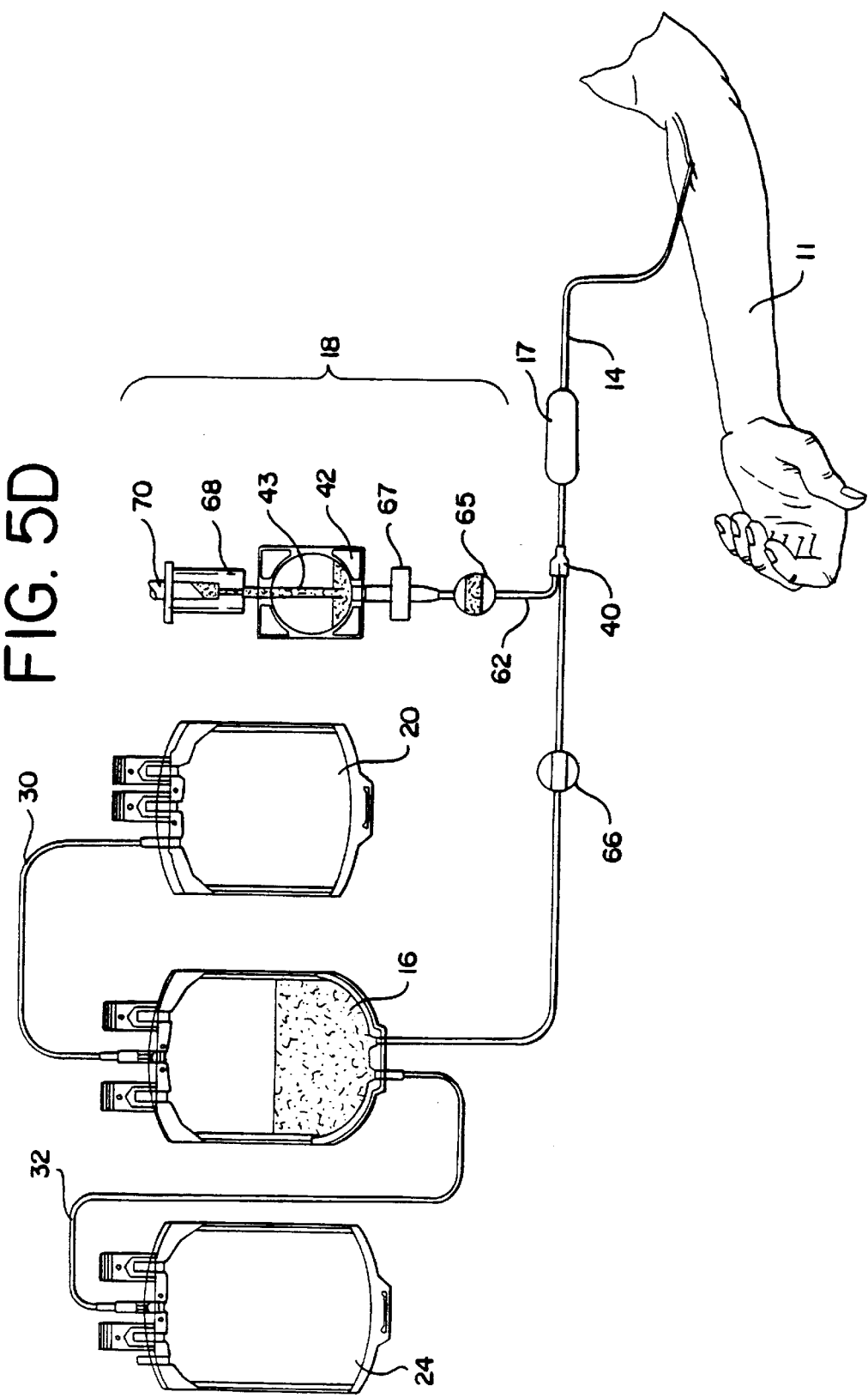

SAMPLING TUBE HOLDER FOR BLOOD SAMPLING SYSTEM

This is a continuation-in-part of U.S. application Ser. No. 09/364,628 filed on Jul. 29, 1999, now U.S. Pat. No. 6,387,086.

BACKGROUND OF THE INVENTION

The administration of blood or blood components often plays a critical role in the emergency and/or long term treatment of patients. Blood or the individual components of blood (such as platelets, plasma, red blood cells, etc.) may be administered or transfused to patients to treat a variety of conditions. For example, blood may be administered to a patient to replace blood lost as a result of trauma, while individual blood components may be administered as part of a longer term treatment of patients suffering from cancer or certain blood related diseases. The blood or blood components administered to the patient come from blood previously collected from donors.

One of the most common blood collection techniques, and perhaps the most well-known, is the "manual" collection of whole blood from healthy donors. As commonly understood and as used herein, "manual" collection refers to a collection method where whole blood is allowed to drain from the donor and into a collection container without the use of external pumps or similar devices. This is in contrast to the so-called "automated" procedures where blood is withdrawn from a donor and further processed by an instrument that typically includes a processing or separation device and pumps for moving blood or blood components into and out of the device.

Regardless of whether the blood collection technique is manual or automated, withdrawing blood from the donor typically includes inserting a vein access device, such as a needle, into the donor's arm (and, more specifically, the donor's vein) and withdrawing blood from the donor through the needle. The "venipuncture" needle typically has attached to it, one end of a plastic tube that provides a flow path for the blood. The other end of the plastic tube terminates in one or more preattached plastic blood containers or bags for collecting the blood. The needle, tubing and containers make up a blood processing set which is pre-sterilized and disposed of after a single use.

In the manual technique, the collection container and plastic tubing may also include a volume of a liquid anticoagulant, while in the automated technique, a separate container of anticoagulant may be provided from which the anticoagulant is metered into the flow path and mixed with the incoming whole blood. In any event, anticoagulant is required because of the tendency of blood to clot and adhere to the walls of the plastic surfaces which it contacts.

An important consideration in any blood collection technique or system is ensuring that the system or set does not become contaminated by airborne bacteria or other foreign substances that may compromise the sterility of the system. Thus, the sterility of the above-described disposable blood processing set or system is maintained by minimizing exposure of the flow paths and interiors of the blood containers to the outside environment. Such systems are commonly referred to as "closed" systems.

After collection but prior to transfusion to a patient, the blood is typically tested for determining blood type and the presence of pathogens such as virus, bacteria and/or other foreign substances in the donor's blood. Typically, testing of the collected blood requires obtaining a sample of the blood from the blood donor at or near the time of collection.

One well-known technique of obtaining a blood sample is to simply withdraw or collect the blood remaining in the flow path of the disposable set after donation. This involves removing the needle from the donor, inserting the needle into a vacuum sealed sampling tube or tube and allowing the blood from the flow path to drain into the tube. However, because there is a limited supply of blood remaining in the flow path, there may not be enough blood to provide enough of a sample to perform all of the required or desired testing. Accordingly, if a larger volume or numerous samples of blood are required, the technician obtaining the sample may continue draining the blood from the tubing, eventually withdrawing the collected anticoagulated blood from the collection container. Withdrawing blood from the collection container, however, may be less desirable in that it may expose the collected blood in the collection container to the outside environment. Withdrawing blood from the collection container for sampling also reduces the volume of available blood for later processing and transfusion.

An alternative to collecting anticoagulated blood from the collection container is to clamp off the flow path near the collection container and divert the blood being withdrawn from the donor to a collection (sampling) tube or tube of the type described above. This procedure typically employs a particular type of disposable tubing set having a preattached sampling site on the main flow path. Blood at or near the sampling site may be obtained by piercing the sampling site with a separately provided needle or other piercing device, and attaching a sampling tube thereto. To minimize the risk that the incoming blood (which is intended for later processing and transfusion) will be exposed to the outside environment, the sample is typically collected after completion of the blood donation.

Still another example of a blood sampling system is described in U.S. Pat. No. 5,167,656, which is assigned to the assignee of the present application. That patent describes a disposable tubing set wherein the flow path includes an enlarged sample collection portion. Blood for sampling is collected in the enlarged portion by clamping off the flow path near the collection container and allowing the enlarged tubing portion to fill with blood. Once the desired volume of blood for sampling is collected in the enlarged tubing portion, the needle is removed from the donor and the blood is transferred to a tube by piercing the cap of the tube with the needle and allowing the blood to drain into the sampling tube.

While these known techniques have generally worked satisfactorily, efforts continue to provide further improvements in the area of blood sampling. For example, as set forth above, the sample is typically obtained after the blood product (intended for further processing and transfusion) has been collected so as to preserve the sterility of the closed system. However, if the donation procedure must be terminated before completion, there may not be an opportunity to obtain a sample directly from the donor. Thus, it would be desirable to provide a sampling system in which blood samples can be obtained either before or after donation, but without the risk of compromising the sterility of the system and/or the collected blood product.

In addition, as discussed above, the use of vacuum-filled tubes or tubes is common in blood sampling processes. When such vacuum-filled tubes are used, there is the possibility that the suction may cause the tubing of the blood processing set to collapse and restrict blood flow. Of even greater concern, particularly in small-veined donors, is the possibility that the suction may cause the donor's vein to collapse. Thus, it would also be desirable to provide a sampling system where the risk of donor vein or tubing collapse is minimized.

It would also be desirable to provide a sampling system which is integrated with the blood collection set and requires few separate or external components.

Finally, where the sampling system includes a holder (with a piercing member) for receiving a sampling tube, it would also be desirable to provide a holder that is compact in size, easily sterilized and reduces the risk that the user will inadvertently come into contact with the sharpened tip of the piercing member within the holder.

SUMMARY OF THE INVENTION

In one aspect, the present invention is embodied in a holder for receiving a blood sampling tube. The holder includes a distal end, a proximal end and a central body portion between the ends. The body portion of the holder defines an interior pocket. The interior pocket may be conformed to receive a sampling tube.

In another aspect, the present invention is embodied in a holder for receiving a sampling tube wherein the holder includes a distal end, a proximal end, a central body portion and a piercing member assembly attachable at the distal end. The assembly has a first portion disposed within the interior pocket and a second portion extending from the distal end to the exterior. The holder also includes a fluid reservoir located at the distal end.

In another aspect, the present invention is embodied in a holder for receiving a sampling tube wherein the holder includes a distal end, a proximal end and a central body portion including at least one tab with an aperture extending therethrough.

BRIEF DESCRIPTION OF THE DRAWINGS

FIG. 1 is a perspective view of a disposable blood collection or processing set including a sampling system embodying the present invention;

FIG. 1A is a perspective view of a portion of an alternative disposable blood collection or processing set including a sampling system embodying the present invention;

FIG. 2A is a perspective view of another variant of a disposable blood collection or processing set including a sampling system embodying the present invention;

FIG. 2C is a perspective view of another variant of a disposable blood collection or processing set including a sampling system embodying the present invention;

FIG. 2D is a perspective view of another variant of a disposable blood collection or processing set including a sampling system embodying the present invention;

FIG. 3 is a perspective view of the sampling system embodying the present invention;

FIG. 4 is a perspective view of the sampling system of FIG. 3 with an another embodiment of the holder;

FIG. 4C is a cross-sectional view of the holder of FIG. 4, taken along 4C—4C;

FIG. 4J is a cross-sectional side view of the holder of FIG. 4F taken along 4J—4J;

FIG. 4K is a cross-sectional side view of the holder of FIG. 4G taken along 4K—4K;

FIG. 4L is a cross-sectional end view of the holder of 4G taken along 4L—4L;

FIG. 5A is a diagram showing one step in the method of obtaining a blood sample in accordance with the present invention;

FIG. 5C is a diagram showing the steps of isolating the blood sampling system from the remainder of the processing set and collecting blood in the collection container; and FIG. 5D is a diagram showing the step of withdrawing the blood sample from the sampling container and collecting it in a sampling tube.

DETAILED DESCRIPTION OF THE DRAWINGS

Figure 2B:
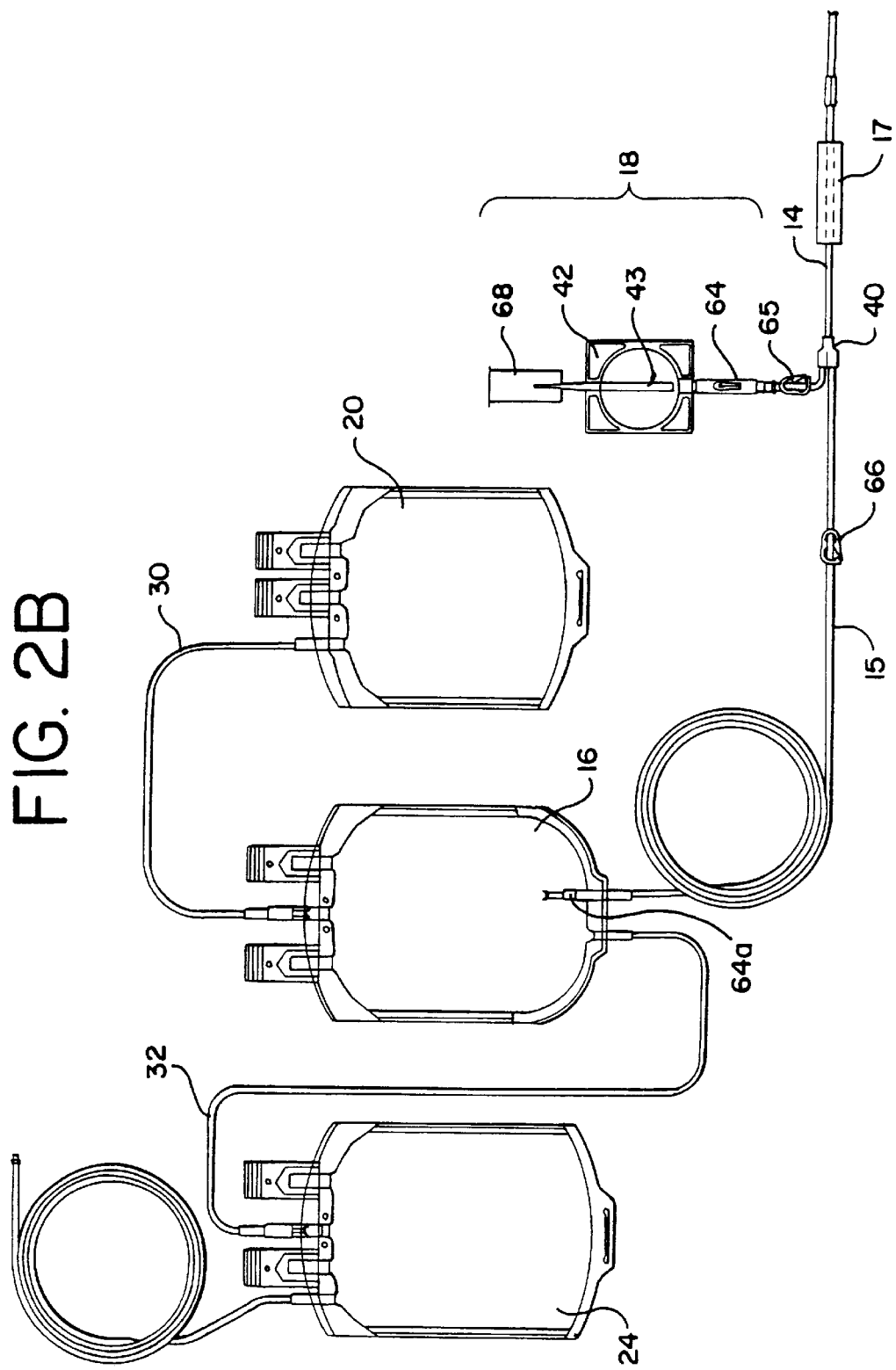
FIG. 2B is a perspective view of another variant of a disposable blood collection or processing set including sampling system embodying the present invention.

Turning now to FIG. 1 of the drawings, the present invention may be embodied in a liquid flow conduit set such as a disposable processing set 10, which is particularly suitable for use in the manual collection of blood from a donor 11. The illustrated disposable set 10 may include a needle such as venipuncture needle 12, and plastic tubings 14 and 15 extending from needle 12 to a collection container such as a flexible plastic container 16. A needle protector 17 may also be provided for retraction and storage of needle 12 after use.

The blood processing set 10 may include a single blood collection container 16 or, more preferably, as shown in FIG. 1, may be a multiple blood container system including additional containers 20 and 24. In accordance with the present invention, disposable processing set 10 includes a sampling system 18, described in more detail below.

As set forth above, blood processing set 10 may include a primary container 16 and one or more integrally attached transfer containers 20 and 24. During use, primary container 16 (sometimes referred to as the donor bag) receives whole blood from the donor through integrally attached donor tubings 14 and 15 and venipuncture needle 12. Container 16 typically includes a suitable anticoagulant such as citrate phosphate dextrose (CPD), citrate phosphate dextrose adenine (CPDA) or acid citrate dextrose (ACD).

Containers 20 and 24 may be attached to primary container 16 by integrally attached transfer tubing 30 and 32. Containers 20 and 24 are provided to receive blood components such as, but not limited to, red blood cells and plasma that have been separated from whole blood. For example, collected whole blood in container 16 may be centrifuged to separate the blood into layers of such components. The heavier cellular components, such as red blood cells, settle to the bottom of the container 16 and the lighter, less dense components, such as plasma (with or without platelets), remain in the top layer. The components may then be separated by expressing the lighter components through transfer tubing 30 and into container 20. Likewise, the heavier components may be expressed through transfer tubing 32 to container 24. Such "top and bottom" separation techniques and disposable processing sets are well known and are available from Baxter Healthcare Corporation of Deerfield, Illinois under the name Optipac®.

Of course, it will be understood that the present invention is not limited to the processing sets shown in the figures and that processing sets having different container and tubing configurations are also within the scope of the present invention. For example, a multiple container system wherein tubing segments 30 and 32 are both attached to container 16 at or near the top of container 16 may also be used. Container 24 may include a volume of a preservative or storage solution which is introduced into container 16 and combined with separated red cells after plasma has been expressed to container 20. Such blood processing sets are also available from Baxter Healthcare Corporation.

Containers 16, 20 and 24 and associated tubing segments of processing set 10 are typically made from conventional and approved medical grade plastic materials. One such material may be polyvinyl chloride that includes a plasticizer such as, but not limited to, plasticizers selected from the family of citrate esters, which are described in U.S. Pat. Nos. 5,167,657, 5,100,401 and 5,026,347, all of which are incorporated by reference herein. Containers made from polyvinyl chloride plasticized with citrate ester or other plasticizers are available from Baxter Healthcare Corporation of Deerfield, Illinois. Alternatively, and depending in part on the blood components to be stored, containers may be made from other materials such as polyolefin materials with or without plasticizer.

Turning now to the sampling system, as shown in FIG. 1, sampling system 18 may be integrally attached to the disposable processing set 10 at Y-connector 40. In general, and as shown in greater detail in FIG. 3, sampling system 18 may include a container 42 having an inlet port 46 and outlet port 50. Container 42 further includes an interior chamber 54 defined by walls 56 and 58 (FIG. 4) that are joined together in a facing arrangement. Walls 56 and 58 may be made from sheets of extruded plastic. Container 42 may be made by heat sealing together walls 56 and 58 or by any other method known to those of skill in the art. Preferably, walls 56 and 58 may joined together by radio frequency (RF) sealing the walls substantially along their peripheries. A bushing 47, (typically made of polyvinyl chloride) may be included at, for example, inlet port 46, and may also be RF sealed to walls 56 and 58.

Container 42 (or the walls 56 and 58) may typically be made of any conventional medical grade plastic material that is sterilizable by known sterilization techniques including autoclaving. One such preferred material is polyvinyl chloride with a plasticizer, such as a citrate ester (e.g. n-butyryltri-n-hexyl citrate), as substantially described above. Of course, other known plasticizers such as TEHTM and DEHP may also be used. In one example, the material used to make walls 56 and 58 may include approximately 70%, by weight, polyvinyl chloride and approximately 30%, by weight, plasticizer.

Container 42 may also include drain tube 43. As shown in FIGS. 3–4, one end of drain tube 43 is attached to container 42 and may provide outlet port 50. Preferably, drain tube 43 may be RF sealed to container walls 56 and 58. Drain tube may be made of any typical medical grade material such as polyvinyl chloride with a plasticizer. Drain tube 43 extends substantially into interior chamber 54 and terminates near inlet port 46. Extending drain tube 43 substantially into interior chamber 54 assures that the end of drain tube 43 will reside within or near the liquid inside container 42, making it less likely that air will be present when liquid (such as blood) is withdrawn from container 42 into a sampling tube. Tube 43 also separates walls 56 and 58 to provide chamber 54 and assists in preventing walls 56 and 58 from collapsing during, for example, heat sterilization. As shown in FIG. 3, in a preferred embodiment, interior chamber 54 may be generally circular. This may allow, for more complete drainage of container 42 by eliminating corners where the blood may be retained. In one embodiment, interior chamber of container 42 may have a volume of approximately 20–50 ml and, more preferably, approximately 30–40 ml.

As further shown in FIG. 3, sampling device 18 may include tubing segment 62 attached to container 42 at inlet port 46. Tubing segment 62 may be attached to container 42 and, more specifically, bushing 47 by, for example, solvent bonding. The other end of tubing segment may be bonded to Y-connector 40. Tubing segments 62 may further include an openable barrier 64 such as a frangible cannula or connector of the type described in U.S. Pat. No. 5,330,464, assigned to the assignee of the present application and incorporated by reference herein. Barrier 64 preserves the sterility of the flow path defined by tubing segment 62. Flow restrictor clamps, such as Roberts clamps 65 and 66 (FIG. 1), on tubing segment 62 and tubing segment 15 may also be provided to allow for flow control through blood processing set 10 by the technician.

Sampling device 18 may further include a receptacle or holder 68 as shown in FIG. 3. As will be described in more detailed below, holder 68 is adapted to receive a blood sampling tube 70. Holder 68 may be attached to container 42 at outlet port 50 to provide an integrated system. In one embodiment, holder 68 includes distal end port 69 which may be mated with and bonded to outlet port 50 prior to heat sterilization. More preferably, distal end port 69 may be bonded to drain tube 43. Subsequent heat sterilization forms a bond between the polycarbonate material of distal end port 69 and, for example, drain tube 43. Of course, other ways of bonding holder 68 to container 42, such as solvent bonding, may also be used. Alternatively, holder 68 may be separately provided and attached to outlet port 50 at the time of use.

In one embodiment (shown in FIG. 3), holder 68 may have a central body portion 71, generally in the shape of a hollow cylinder. Holder 68 is open at its proximal end to allow for insertion of sampling tube 70. Holder 68 may be made of any plastic sterilizable material. Holders of the type generally discussed above are available from, for example, Becton-Dickinson Co. of Franklin Lakes, N.J.

Holder 68 may include a piercing member 74 as generally shown in FIG. 3 (or FIG. 4 and 4C). Piercing member 74 may be a needle, cannula or other biocompatible device having a sharpened tip. As set forth above, piercing member 74 includes a piercing end 76. Piercing member 74 may be made of any material of sufficient strength such as metal or plastic. In addition, end 76 of piercing member 74 may be enclosed within a protective sheath 80 (best shown, for example, in FIG. 4C). Protective sheath 80 may preferably be made of a flexible material, such as latex, which is capable of being penetrated by the tip of piercing member end 76. Also protective sheath 80 should be sufficiently resilient to return to its original shape (covering end 76) upon withdrawal of sampling tube 70.

In an alternative embodiment, holder 68 may be provided with an interior pocket which may be conformed to receive the sampling tube, as generally shown in FIG. 4. As shown in FIG. 4E, holder 68 may include a proximal end 110, a distal end portion 114 and a generally rectangular central body portion 118 having oppositely facing walls 78a and 78b (FIG. 4G), which define an interior pocket 81. Walls 78a and 78b are longitudinally hinged or creased to allow for flexing of holder 68 as shown in FIG. 4A. More specifically, as shown in FIG. 4F, each of the facing walls 78a and 78b may include a central longitudinal hinge 122 and 126 respectively near the central axis of each of the walls. In addition, body portion 118 may include longitudinal hinges 130, 134, 138 and 140 spaced from central longitudinal hinges 122, 126 and located near the peripheral edges of walls 78a and 78b, as perhaps best seen in FIGS. 4G and 4L. In one embodiment, the central longitudinal hinge 122 and the peripheral hinges 130, 134, 138 and 142 may be provided as thinned areas (i.e., areas of reduced thickness) of the walls 78a and 78b. For example, whereas walls 78a and 78b may typically have a thickness of between approximately 0.6–1.0 mm, the thickness of the walls at hinges 122, 126, 130, 134, 138 and 140 may typically be between approximately 0.2–0.4 mm. In any event, the hinges of walls 78a and 78b allow interior pocket 81 to be conformed from a "closed" position as shown in FIG. 4F to an "open" position as shown in FIG. 4G.

Figure 4A:
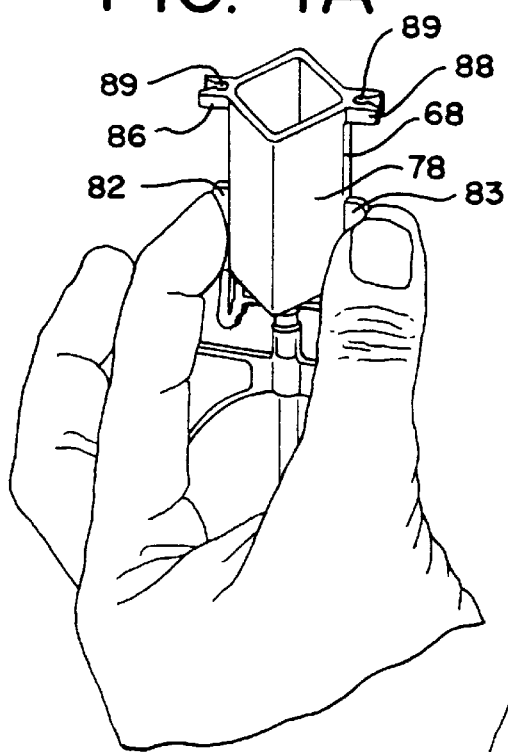
FIG. 4A is a perspective view of the sampling system of FIG. 4 with the holder open.
Figure 4B:
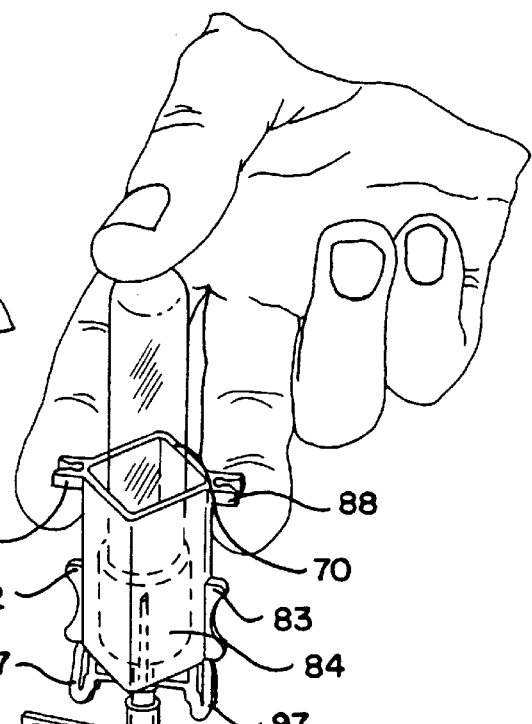
FIG. 4B is a perspective view of the sampling system of FIG. 4 with the sampling tube disposed within the holder.
Figure 4D:
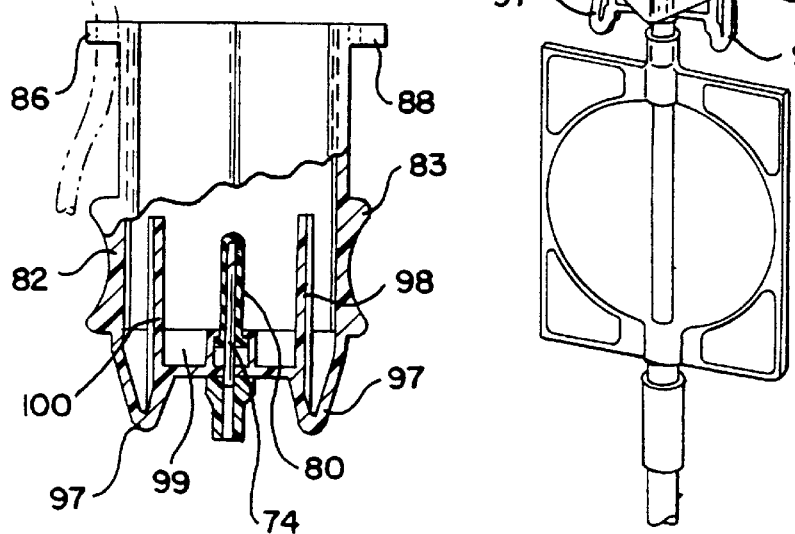
FIG. 4D is a partial cross-sectional view of the holder of FIG. 4 with a portion broken away to show the interior of the holder.
Figure 4E:
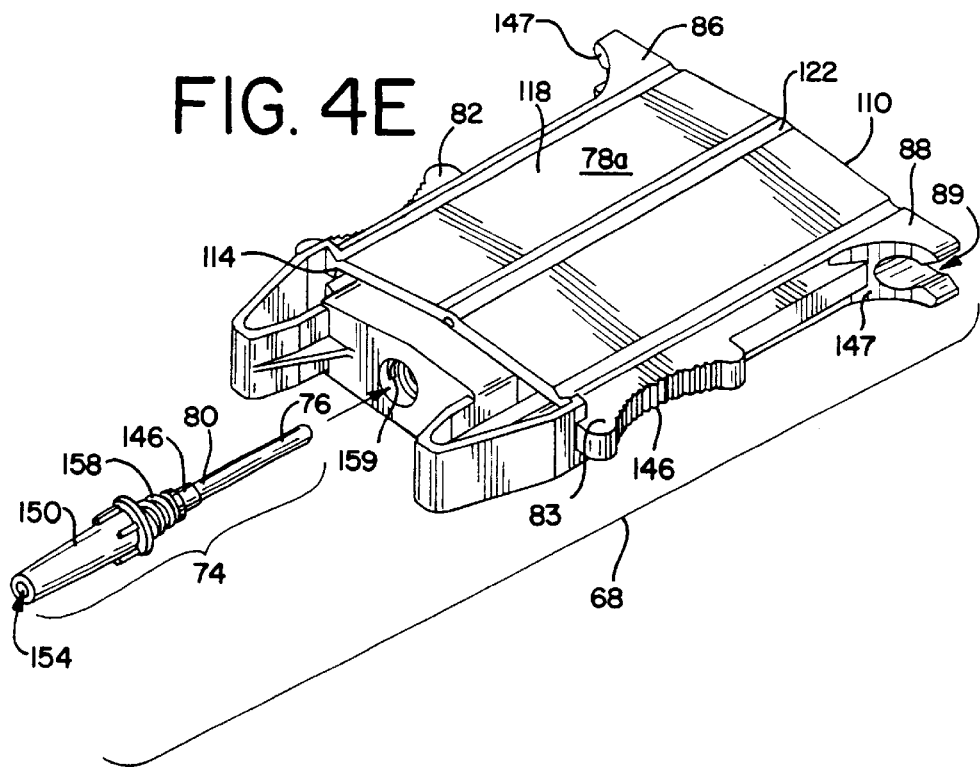
FIG. 4E is a perspective view from the distal end of a holder embodying the present invention with an attachable piercing member assembly.
Figure 4F:
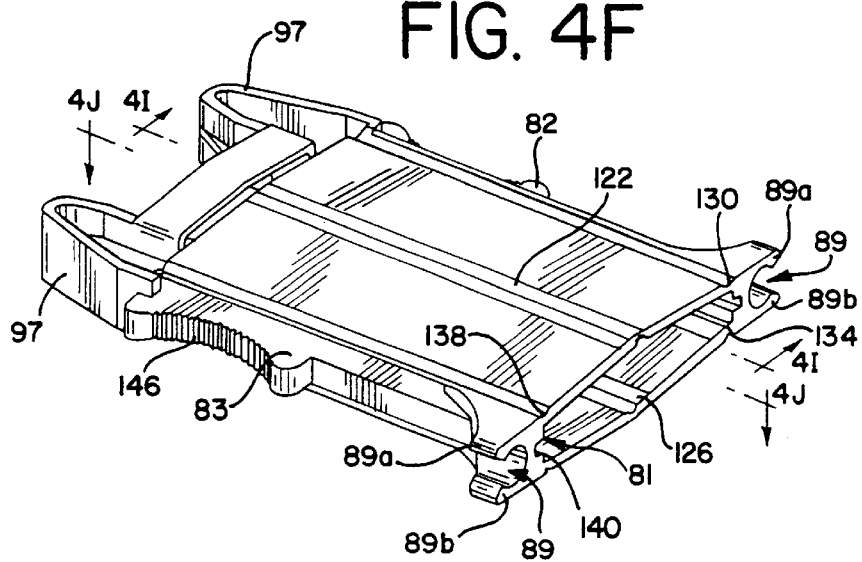
FIG. 4F is a perspective view from the proximal end of a holder embodying the present invention.
Figure 4G:
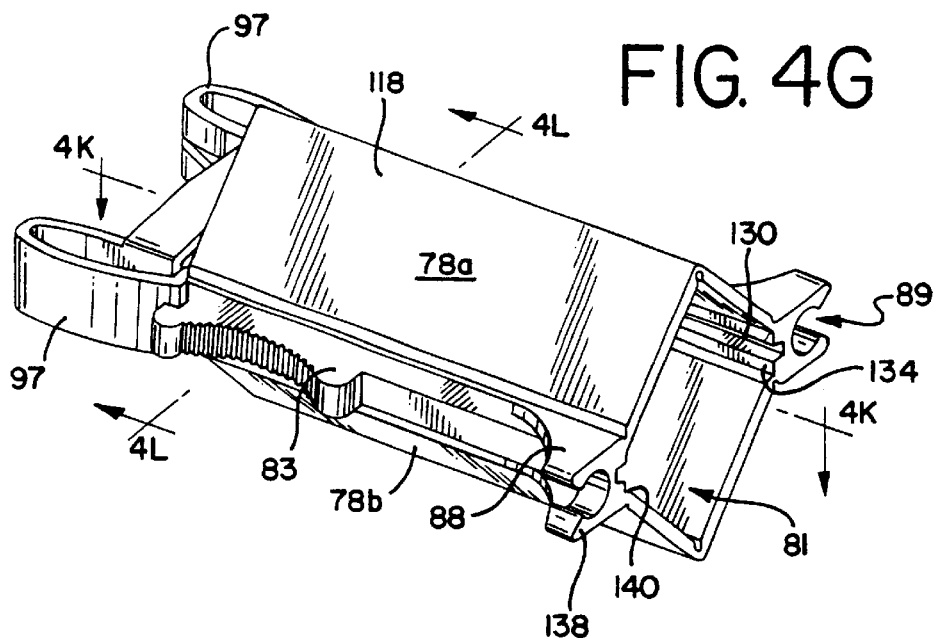
FIG. 4G is a perspective view from the proximal end of the holder of FIG. 4F in an open position.
Figure 4H:
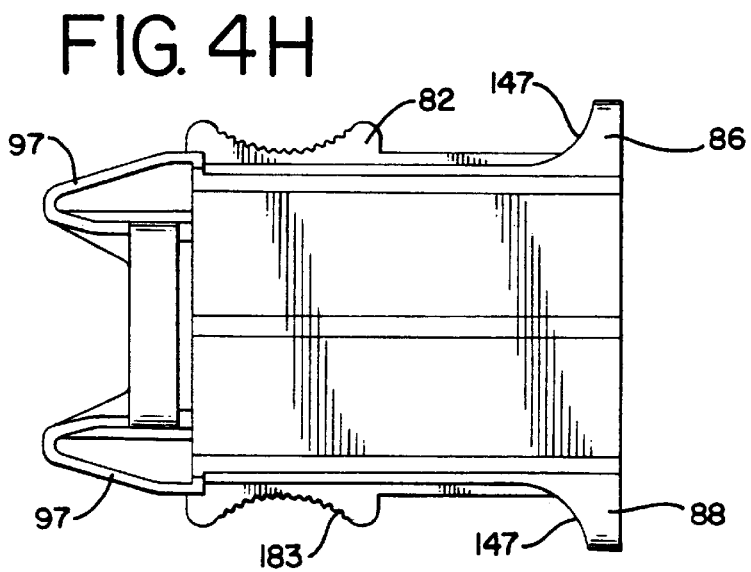
FIG. 4H is a plan view of the holder embodying the present invention.
Figure 4I:
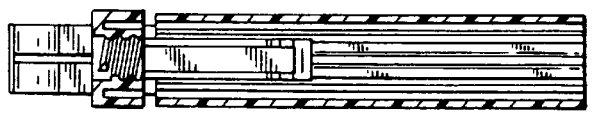
FIG. 4I is a cross-sectional side view of the holder of FIG. 4F taken along 4I—4I.

In a preferred embodiment, walls 78a and 78b may include pinching tabs 82 and 83 for compression by the technician to conform and flex open interior pocket 81 as generally shown in FIG. 4A. Pinching tabs 82 and 83 may be generally concave and include ridges 146 to provide gripping surfaces for the user. As shown in FIG. 4E and more clearly in 4J, pinching tabs are joined to springs 97, so that springs 97 are compressed when pinching tabs are squeezed, but return to their normal expanded position when pressure on the tabs 82 and 83 is withdrawn. This returns holder 68 to its "closed" position (which protects the user from the possibility of an accidental needle stick).

Holder 68 shown in FIGS. 4–4L may further include finger grasping tabs 86 and 88. Finger grasping tabs 86 and 88 provide grasping areas for the operator when inserting sample tube 70 as shown in FIG. 4B. The bottom grasping surface 147 of tabs 86 and 88 may be generally straight and forms a right angle with central body portion 118 as shown in FIG. 4–4D or, more preferably, curved for easier and more comfortable grasping by the user, as shown in FIGS. 4E–4L. Turning now to FIG. 4B and 4E, finger grasping tabs 86 and 88 may further include apertures 89 for retaining tubing segments before, during and after use of disposable processing set 10. The diameter of apertures 89 should be sufficient to receive the tubing of the blood processing set. Apertures 89 are defined by a pair of jaws 89a and 89b (FIG. 4F) which are partially separable to allow the tubing to be inserted into apertures 89.

In addition, holder 68 shown in FIGS. 4–4L may further include positioning prongs 98 and 100. Positioning prongs 98 and 100 are laterally spaced relative to piercing member 74 and assist in guiding tube 70 over piercing member 74. Positioning prongs 98 and 100 also limit the degree of flexing so that when holder 68 is flexed to the open position, interior pocket 81 provides a generally square cross-sectional area sufficient to allow insertion of the cylindrical sampling tube. Holder 68 shown in FIGS. 4–4D may further include a reservoir 99 to retain any uncollected drops of blood.

As shown in FIG. 4, holder 68 may include a piercing member assembly 74. Piercing member 74 may be integral with holder 68 or, as shown in FIG. 4E, may be attachable to holder 68. In any event, piercing member 78 may be or may include a needle, cannula or other biocompatible device having a sharpened tip.

As shown in FIG. 4E, piercing member assembly 74 includes a first proximal piercing end 76 attached to a hub 146. The opposite, distal end of piercing member assembly 74 includes luer 150 with a fluid passageway 154 provided inside luer 150. Where piercing member 74 is attachable to holder 78, it may further include means for attaching piercing member assembly 74 to holder 68. As shown in FIG. 4E, for example, piercing member 74 may include a threaded portion 158. Accordingly, holder 68 may include a threaded slot 159 to receive the threaded portion 158 of piercing member 74. This allows piercing members to be securely screwed into holder 68.

As described above, piercing member assembly 74 and, more particularly, the proximal portion of piercing member, may be made of any material of sufficient strength such as metal or plastic. In addition, end 76 of piercing member 74 may be enclosed within a protective sheath 80 (FIG. 4E). Protective sheath 80 may preferably be made of a flexible material, such as latex, which can be penetrated by the tip of piercing member end 76. Also, as previously described, protective sheath 80 should be sufficiently resilient to return to its original shape (covering end 76) upon withdrawal of sampling tube 70. The remainder of piercing member, namely, luer 150 and threaded portion 158 may be made of any suitable, heat or radiation (gamma or electron beam) sterilizable plastic such as polycarbonate. At least luers 150 should be made of a material capable of being bonded, such as by solvent bonding or heat sealing, to the tubing of processing set 10 such as drain tube 43 at, for example, outlet port 50.

The holder 68 described above and shown in FIGS. 4–4L provides several benefits. From the manufacturing standpoint, for example, the flat shape of holder 68 (when in the closed "position") makes for more efficient packaging by allowing more units to be packaged per case. For example, when in the "closed" position, holder may have a width of approximately 10 mm or less. Additionally, the flat shape of holder 68 provides for a shorter heat sterilization cycle (i.e., by reducing the thickness of the holder). From the user's standpoint, the flat shape of holder 68 (when in the closed position) protects the user from accidental needle sticks by limiting access to the interior pocket. The limited thickness also reduces waste volume.

Holder 68 may also serve as a receptacle for holding a needle protector (with retracted venipuncture needle therein) after completion of the blood donation. Use of the holder in this manner is described in pending U.S. patent application Ser. No. 09/442,210, filed Nov. 17, 1999, which is incorporated by reference herein.

The holder shown in FIGS. 4–4L may be made of any suitable, biocompatible, flexible and sterilizable (either by heat or radiation such as gamma or electron beam radiation) material such as polyolefin, and preferably polypropylene or polyethylene, including high-density polyethylene.

Holder 68 of FIG. 4 may typically be made by casting, injection molding or other techniques known to those of skill in the art. As in the embodiment of FIG.3, the holder shown in FIGS. 4–4D may also include a distal end port 69 made, for example, of polycarbonate or other suitable material, that may be bonded to outlet port 50 and/or drain tube 43 during heat sterilization. More, preferably, the distal end port is the distal portion of piercing member assembly 74 e.g., (luer 150) described above, which portion may be bonded to outlet port 50 and/or drain tube 43 during heat sterilization. Of course, other ways of bonding holder 68 to container 42 may also be used.

During a collection procedure, a sampling tube 70, as shown in FIG. 3, may be inserted into the interior of holder 68. As shown in FIGS. 3 and 4B, tube 70, which is typically a vacuum sealed tube, may itself include a piercable cap 84. Such tubes are available from the Becton-Dickinson Co. of Franklin Lakes, N. J. and are sold under the trade name VACUTAINER®.

Figure 5B:
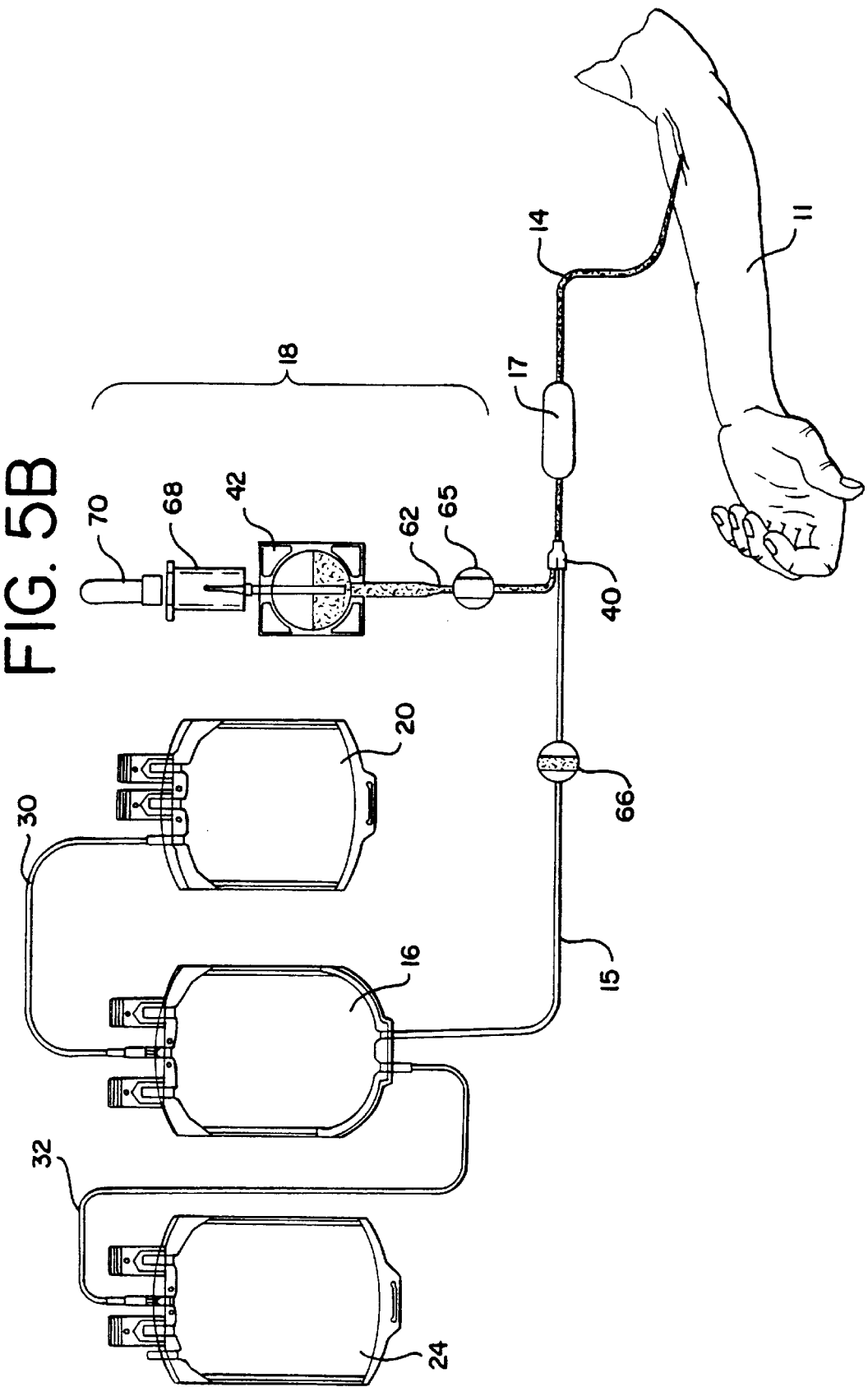
FIG. 5B is a diagram showing the step of collecting a blood sample in accordance with the present invention.

The method of collecting a blood sample from a donor during a blood donation using the blood processing system generally described above will now be described. In one embodiment, at the outset of the donation procedure, disposable processing set 10 may be provided with clamps 65 and 66 in a closed position, as shown in FIG. 5A. Next, frangible connector 64 is opened and needle 12 is inserted into the arm of the donor 11. As shown in FIG. 5B, clamp 65 is opened and container 42 is allowed to fill with the blood from the donor. Alternatively, clamp 65 may be opened prior to venipuncture.

Once a sufficient volume of blood for sampling has been collected, sampling system 18 may be isolated from the remainder of the processing set 10 by heat sealing tubing segment 62 in ways that are known to those of skill in the art. One device that may be used for sealing is the tubing sealing device known as the Hematron®, sold by Baxter Healthcare Corporation. Alternatively, line 62 may be sealed by a metal retaining clip or other means known to those of skill in the art. After isolation by seal 67, clamp 65 is closed and the clamp 66 is opened to allow blood flow into container 16 as shown in FIG. 5C. Of course, it will also be appreciated by those of skill in the art that, clamp 65 may be closed and clamp 66 may be opened (to allow blood flow into container 16) before heat sealing tubing segment 62.

In any event, once sampling system 18 has been isolated from the remainder of the blood processing set 10, blood collected in container 42 may be transferred to a sampling tube 70 as shown in FIG. 5D and in more detail in FIGS. 3 and 4C. Sampling tube 70 is inserted into the interior of holder 68 so that cap 84 of tube 70 is pierced by the piercing end 76 of piercing member 74, as generally shown in FIG. 4B. As shown in FIGS. 3 and 4, it is preferred that sampling tube 70 be introduced into holder 68 in an inverted position so that blood flows up into tube 70. Applicants have discovered that such blood flow results in less hemolysis of red blood cells as compared to other collection techniques where the blood is allowed to drip into an upright tube.

Finally, turning briefly to FIGS. 1A and 2A–2D, the blood processing sets shown therein are variants of the processing set 10 of FIG. 1. While the sampling system 18 shown in these embodiments is similar to the sampling system described above, the processing sets differ, in general, in the location of openable barriers 64, the orientation of certain components and the like. For example, the blood processing set shown in FIG. 1A is virtually identical to the set of FIG. 1 with the exception that Y-connector 40 is oriented in the opposite direction (which may be desirable for packaging purposes).

In FIG. 2A, an additional openable barrier 64 of the type described above may be included on line 15. Inclusion of barrier 64 on line 14 may prevent additional anticoagulant from entering line 14 distal to Y-connector 40. A similar but alternative embodiment is shown in FIG. 2B where an openable barrier 64a (such as a polyvinyl chloride frangible cannula) is located near the inlet port of container 16. In these embodiments, barrier 64 or 64A would be opened just prior to collection of blood in container 16.

In another embodiment, shown in FIG. 2C, an openable barrier 64 may be included on line 14, but not on line 62. In this embodiment, holder 68 preserves the sterility of the system. Finally, as shown in FIG. 2D, a Y-connector of the type described in U.S. Pat. No. 5,372,143, which is incorporated by reference herein, may be used in combination with the sampling system 18 of the present invention.

The disposable processing set and sampling system of the present invention provide many benefits. One benefit is that a blood sample may be obtained prior to the donation while still preserving the sterility of flow path between the donor and collection container. Specifically, as described above, a blood sample may be collected in container 42, which container may then be isolated from the remainder of the system (by, for example, sealing or clipping). Once container 42 has been isolated, a sampling tube may be introduced into the holder of the sampling system without the risk that bacteria or other foreign substances on the tube will contaminate the rest of the blood processing set, including flow path 14.

An advantage of pre-donation sampling is that bacteria or foreign substances that may be present on the donor's skin will not be transmitted to collection container 16, but will be diverted to sampling container 42.

Another advantage of pre-donation sampling is that it allows for collection of sample for testing, even if the donation is not completed.

Another advantage of pre-donation sampling is that it may provide a more accurate profile of the donor's blood, particularly regarding the hemoglobin level of the donor. For example, during donation, the loss of blood volume in the donor is compensated by plasma. This compensation by plasma typically lowers the hematocrit of the donor's blood. If the sample is taken after donation, the donor hematocrit may be lower (by possibly as much as 0.5 g/dL) than it otherwise would be if the sample is collected prior to donation.

The present invention provides additional advantages, whether used for pre-donation or post-donation sampling. One advantage is the reduced risk of tubing or donor vein collapse as described above. Container 42 acts as a buffer between the sampling tube and tube or vein. Thus, any suction forces generated by introduction of the vacuum sealed tube will be absorbed by the container 42 and not tube or donor vein.

Of course, there may be other advantages of the present system not discussed herein which will be apparent to those of skill in the art.

The present invention has been described in accordance with the preferred embodiments. However, it will be understood that minor variations to the embodiments shown herein may be made without departing from the present invention which is specifically set forth in the appended claims.

That which is claimed:

1. A holder for receiving a sampling tube, said holder comprising a distal end, a proximal end and a central body portion between said distal and proximal ends, said body portion comprising at least two opposed flexible walls defining an interior pocket, a piercing member substantially within the interior pocket, a pair of opposed pinching tabs, wherein each of said tabs is joined with each of said opposed walls;

whereby said interior pocket may be conformed to receive a sampling tube by applying pressure to said pinching tabs.

2. The holder of claim 1 wherein said walls are hinged to allow said interior pocket to be conformed.

3. The holder of claim 2 wherein each of said two opposed flexible walls includes a central longitudinal hinge.

4. The holder of claim 1 wherein each of said walls include one, or more hinges spaced from said central hinge.

5. The holder of claim 1 wherein said interior pocket comprises a generally rectangular cross-sectional area.

6. The holder of claim 1 wherein the distance between said opposed flexible walls is approximately 10 mm.

7. The holder of claim 1 comprising a pair of positioning prongs disposed within said interior pocket spaced from the central axis of said holder.

8. The holder of claim 1 wherein said pinching tabs include ridges to provide finger gripping surfaces.

9. The holder of claim 8 wherein said pinching tabs are generally concave.

10. The holder of claim 1 wherein said piercing member is attached to said holder at said distal end.

11. The holder of claim 1 wherein said piercing member is integral with said holder.

12. The holder of claim 1 wherein said piercing member is separately attachable to said holder.

13. The holder of claim 1 wherein said distal end is open, said holder further comprising a fluid receptacle distal to said open distal end.

14. The holder of claim 1 comprising compressible springs to allow for conforming of said interior pocket.

15. The holder of claim 14 wherein said finger grasping tabs comprise a pair of jaws defining an aperture, wherein said jaws are partially separable to allow for insertion of a length of cylindrical tubing within said aperture.

16. The holder of claim 1 comprising at least one tab located near said proximal end of said holder, said tab including an aperture extending therethrough, said aperture adapted for holding a length of cylindrical tubing.

17. The holder of claim 16 wherein said tab includes a generally flat top surface and a curved bottom surface.

18. The holder of claim 1 wherein said holder is made from a thermoplastic material.

19. The holder of claim 18 wherein said thermoplastic material is selected from the group consisting of polyethylene and polypropylene.

20. The holder of claim 18 wherein said polyethylene is a high density polyethylene.

21. The holder of claim 1 wherein said holder is made of a material capable of being sterilized by at least steam or gamma radiation.

22. A holder for receiving a sampling tube, said holder comprising an open distal end, an open proximal end, a central body portion defining an interior pocket, a piercing member assembly attachable to said holder, and a fluid reservoir distal to said open distal end said body portion comprising at least two opposed-flexible walls defining an interior pocket and a pair of pinching tabs, wherein each of said pinching tabs is joined with each of said opposed walls.

23. The holder of claim 22 wherein said piercing member assembly is attached to holder at said fluid reservoir and extends into said interior pocket.

24. The holder of claim 22 wherein said first portion of said piercing member assembly comprises a sharpened tip enclosed within a flexible sheath and said second portion includes a luer in flow communication with said first portion.

25. The holder of claim 22 wherein said body portion comprises a pair of oppositely facing walls and a pair of opposed pinching tabs joined with said walls.

26. The holder of claim 25 comprising a pair of guiding prongs attached to said fluid reservoir and extending into said interior pocket.

* * * * *